(12) United States Patent
Fieselmann

(10) Patent No.: US 11,357,475 B2
(45) Date of Patent: Jun. 14, 2022

(54) DEVICE AND METHOD FOR ULTRASOUND EXAMINATION

(71) Applicant: SIEMENS HEALTHCARE GMBH, Erlangen (DE)

(72) Inventor: Andreas Fieselmann, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 315 days.

(21) Appl. No.: 15/963,488

(22) Filed: Apr. 26, 2018

(65) Prior Publication Data

US 2018/0310910 A1 Nov. 1, 2018

(30) Foreign Application Priority Data

Apr. 26, 2017 (EP) ..................... 17168227

(51) Int. Cl.
*A61B 8/00* (2006.01)
*A61B 6/00* (2006.01)
(Continued)

(52) U.S. Cl.
CPC .......... *A61B 8/4416* (2013.01); *A61B 6/4411* (2013.01); *A61B 6/4417* (2013.01); *A61B 6/4464* (2013.01); *A61B 6/4476* (2013.01); *A61B 6/54* (2013.01); *A61B 6/547* (2013.01); *A61B 8/4218* (2013.01); *A61B 8/4254* (2013.01); *A61B 8/4411* (2013.01); *A61B 8/54* (2013.01); *A61B 6/08* (2013.01); *A61B 6/4452* (2013.01); *A61B 6/4458* (2013.01); *A61B 6/5247* (2013.01); *A61B 8/429* (2013.01); *A61B 8/5261* (2013.01)

(58) Field of Classification Search
CPC ..... A61B 8/4416; A61B 8/429; A61B 8/4411; A61B 8/4218; A61B 6/4417
See application file for complete search history.

(56) References Cited

U.S. PATENT DOCUMENTS 5,222,484 A * 6/1993 Krauss ............... A61B 17/2251
378/62
5,388,581 A * 2/1995 Bauer ................ A61B 17/2255
378/162

(Continued)

FOREIGN PATENT DOCUMENTS

CN 101610721 A 12/2009
DE 1021102 A1 1/1991
(Continued)

OTHER PUBLICATIONS

Shung, K. Kirk, "Diagnostic Ultrasound: Imaging and Blood Flow Measurements". Taylor & Francis Group, LLC. Boca Raton, FL. 2006. (Year: 2006).*

(Continued)

*Primary Examiner* — Colin T. Sakamoto
(74) *Attorney, Agent, or Firm* — Laurence A. Greenberg; Werner H. Stemer; Ralph E. Locher

(57) ABSTRACT

With a device and an associated method, an ultrasound unit is coupled with a coupling unit to an existing x-ray unit. The ultrasound unit is guided with the aid of controllable elements of a positioning unit of the x-ray unit on a patient for an ultrasound examination. In this manner X-ray recordings and ultrasound recordings of an object can be produced.

3 Claims, 3 Drawing Sheets

(51) Int. Cl.
    *A61B 6/08*     (2006.01)
    *A61B 8/08*     (2006.01)

(56) References Cited

U.S. PATENT DOCUMENTS

| | | | | |
|---|---|---|---|---|
| 5,488,951 | A * | 2/1996 | Bauer | A61B 6/12 378/162 |
| 5,697,480 | A * | 12/1997 | Herbermann | B25J 19/063 192/150 |
| 5,954,446 | A * | 9/1999 | Ireland | B23K 9/32 403/11 |
| 5,983,123 | A * | 11/1999 | Shmulewitz | A61B 6/50 128/915 |
| 6,119,034 | A * | 9/2000 | Herrmann | A61B 17/2255 600/427 |
| 6,425,865 | B1 | 7/2002 | Salcudean et al. | |
| 2003/0167004 | A1 | 9/2003 | Dines et al. | |
| 2005/0113684 | A1 * | 5/2005 | Lokhandwalla | G01H 3/00 600/427 |
| 2005/0226377 | A1 * | 10/2005 | Wong | A61N 5/10 378/65 |
| 2007/0167806 | A1 * | 7/2007 | Wood | A61B 8/13 600/459 |
| 2007/0263768 | A1 * | 11/2007 | Ullberg | A61B 8/4416 378/63 |
| 2010/0041991 | A1 | 2/2010 | Roundhill | |
| 2012/0083692 | A1 * | 4/2012 | Stoll | A61B 8/0858 600/437 |
| 2014/0180082 | A1 | 6/2014 | Evans et al. | |
| 2014/0348303 | A1 * | 11/2014 | Ham | G03B 42/047 378/189 |
| 2016/0310221 | A1 * | 10/2016 | Bar | A61B 34/20 |
| 2018/0289445 | A1 * | 10/2018 | Krinninger | A61B 34/25 |
| 2018/0360400 | A1 * | 12/2018 | Simon | A61B 8/4416 |
| 2020/0022860 | A1 * | 1/2020 | Van Doorn | A61B 90/57 |

FOREIGN PATENT DOCUMENTS

| | | |
|---|---|---|
| DE | 4021102 A1 | 1/1991 |
| EP | 1405604 A1 | 4/2004 |
| EP | 2853200 A1 | 4/2015 |
| JP | 5641676 B2 | 12/2014 |
| KR | 20140057504 A | 5/2014 |

OTHER PUBLICATIONS

ABC News "Remote ultrasound robot that give operator sense of touch pioneered by scientists" First posted May 20, 2016 by Geelong reporter Cameron Best // https://www.abc.net.au/news/2016-05-20/remote-ultrasound-robots-give-operator-sense-of-touch-developed/7433598.

American Institute of Ultrasound in Medicine (AIUM) "Transducer Manipulation", AIUM Technical Bulletin, Journal of Ultrasound in Medicine, vol. 18, No. 2, pp. 169-175, Feb. 1999 // https://doi.org/10.7863/jum.1999.18.2.169.

RSNA "Telerobotic Ultrasound May Revolutionize Telemedicine" RSNA News, vol. 25, No. 12, pp. 9-10, Dec. 2015.

* cited by examiner

DEVICE AND METHOD FOR ULTRASOUND EXAMINATION

CROSS-REFERENCE TO RELATED APPLICATION

This application claims the priority, under 35 U.S.C. § 119, of European application EP 17168227.1, filed Apr. 26, 2017; the prior application is herewith incorporated by reference in its entirety.

BACKGROUND OF THE INVENTION

Field of the Invention

In order to locate and verify pathological symptoms of an organ of a patient, for instance, different imaging methods are often required in order to generate images of a region of a patient. For the initial diagnosis, ultrasound recordings as well as individual or 3D x-ray recordings could be produced, for instance. The disadvantage with the different recordings is that these are produced by two separate recording systems. Therefore in addition to controllable and exactly alignable x-ray recording units, individual x-ray recordings or a series of x-ray recordings of regions of a patient to be examined are generated and in addition to this in a subsequent work step, ultrasound recordings are recorded with an ultrasound unit which is guided or is to be aligned manually. A possible assignment of abnormalities in the x-ray or ultrasound image is down to the judgment of the treating physician.

SUMMARY OF THE INVENTION

The object underlying the present invention is to specify a device and a method, with which at least two different image recording methods are possible.

With the subject matter of the invention, a device and an associated method are present, in which x-ray recordings of an object can be produced with an x-ray unit, wherein the x-ray unit can be aligned with the object using an alignable positioning unit. With this device and the associated method, provision is made for an ultrasound unit for producing ultrasound recordings, wherein the ultrasound unit is aligned with the object using the positioning unit of the x-ray unit.

The invention is advantageous in that the x-ray and ultrasound images are generated using a device and an associated method, wherein in each case the same coordinate system forms the basis of the images to be generated.

The invention is advantageous in that the features in the x-ray and ultrasound image can be related to one another.

The invention is advantageous in that both the ultrasound unit and the x-ray unit can be used as a telemedical apparatus.

The invention is advantageous in that the kinematics of the positioning unit of an existing x-ray unit is used for the alignment or guidance of an ultrasound unit.

The invention is advantageous in that the remote-controllable positioning unit takes the pressure off a physician.

The invention is advantageous in that images can be generated with different contrasts, wherein soft tissue and bones can be easily seen in the ultrasound image and the x-ray image, respectively.

Other features which are considered as characteristic for the invention are set forth in the appended claims.

Although the invention is illustrated and described herein as embodied in a device and a method for ultrasound examination, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The subject matter of the invention forms a device and an associated method for x-ray and/or ultrasound examination in which an ultrasound unit can be fastened with a coupling unit to an x-ray unit. The x-ray unit is positioned and aligned using a positioning unit. In one embodiment variant, the positioning unit has the controllable axes required to position and control the x-ray unit. The ultrasound unit is positioned on the patient using the positioning unit of the x-ray unit and is guided or aligned in accordance with the control commands input on a control element by an assistant or a physician. To align the ultrasound unit in a non-restrictive manner, the positioning unit has a plurality of degrees of freedom.

Figure 1:
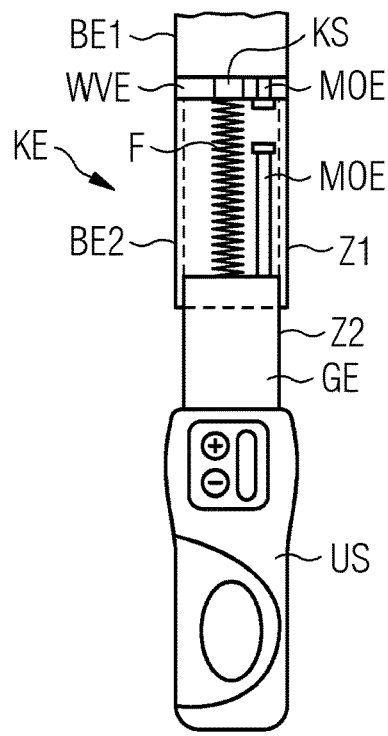
FIG. 1 is a diagrammatic, front view of an ultrasound unit with a coupling unit according to the invention.

Referring now to the figures of the drawings in detail and first, particularly to FIG. 1 thereof, there is shown an ultrasound unit US with a coupling unit KE. In this embodiment and view, the coupling unit KE is made up of a first fastening unit BE1 and a second fastening unit BE2. An active connecting element unit WVE is arranged between the first and the second fastening unit BE1, BE2. While the first fastening unit BE1 has fastening-specific elements for a support or docking stations provided especially on the x-ray and/or the positioning unit P, the second fastening unit BE2 is embodied such that this is made up of a first and second hollow body Z1, Z2, for instance. The second hollow body Z2 can be integrated by way of guide elements into the first hollow body Z1 or can be inserted herein. The accommodation of the second hollow body Z2 in the interior of the first hollow cylinder Z1 is regulated by way of at least one damping element. In this embodiment variant, a spring F arranged in the first hollow body Z1 is provided as a damping element. The ultrasound unit US is arranged at the open end of the second hollow body Z2. An active connecting element unit WVE, which permits a tolerance-free connection between both fastening units BE1, BE2, is embodied between the first and second fastening unit BE1, BE2. The insertion of the second hollow body Z2 into the first hollow body Z1 is absorbed by the spring F arranged in the interior of the first hollow body Z1, as specified above. The spring force of the compressing spring F is captured by way of a force sensor KS. If the spring force of the compressing spring F exceeds a predeterminable value, the active connecting element unit WVE is embodied such that the previously connected first and second fastening element BE1, BE2 separate. In this embodiment variant a further mechanical securing unit MOE is integrated in the first hollow body Z1. This mechanical securing unit MOE is embodied such that once the second hollow body Z2 has covered a distance in the first hollow body Z1, an opening mechanism in the active connecting element unit WVE is actuated and the first is separated from the second fastening unit BE1, BE2. In a further embodiment variant, the first fastening unit BE1 of the coupling unit KE can be omitted and the active connecting element unit WVE is directly connected with a corresponding docking station provided herefor on the x-ray unit R and/or positioning unit P.

Figure 2:
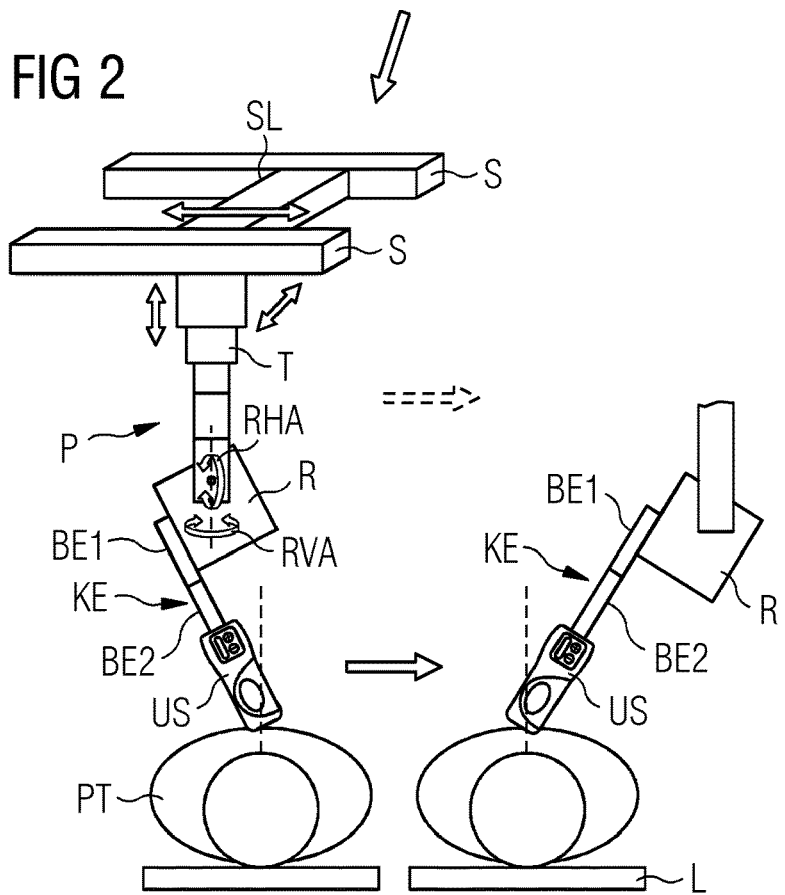
FIG. 2 is a schematic view of a device combination.

FIG. 2 shows a schematic representation of an x-ray system. A device combination containing ultrasound unit US and x-ray unit R is arranged on this x-ray system. The ultrasound unit US is fastened with a coupling unit KE to the x-ray unit R. In this embodiment variant, the x-ray unit R can be aligned by way of a carriage SL guided on rails S and a telescopic arm T which can be moved on the carriage SL in the space toward a positioned object or patient PT. In this embodiment variant, the first fastening unit BE1 of the coupling unit KE can be fastened to docking stations or coupling stations provided herefor on the x-ray unit R. The carriage SL can be moved along the rail system S fastened on a ceiling, for instance. The telescopic arm T which can be varied in terms of length can be moved at right angles to the direction of movement of the carriage SL. An alignable unit having a plurality of controllable axes is arranged at the end of the telescopic arm T. The x-ray unit R is then fastened to this unit. A patient PT positioned on a couch, for instance, is shown. If an ultrasound examination is to be generated with ultrasound recordings of a region of a patient PT, the ultrasound unit US fastened to a coupling unit KE is fastened to docking stations provided herefor on the x-ray unit R or the positioning unit P. According to an ultrasound examination to be carried out, the ultrasound unit US is positioned on a specific area of the patient PT and the ultrasound recording is generated by tilting or twisting or swiveling the ultrasound unit US. The assistant or physician controls the positioning unit P by way of a control element. The control functions triggered by the control unit are converted by way of a control unit, not shown explicitly here, into control pulses for individual, electronically controllable electric motors in the positioning unit P in order to bring about an intended targeted alignment of the ultrasound unit US. A possible starting position or an initial alignment of the ultrasound unit US and a possible end position of the ultrasound unit US on the patient PT are shown in FIG. 2. In order to achieve this positioning of the ultrasound unit US, the carriage SL is moved, for instance according to the direction of movement indicated, while the extended telescopic arm T is slightly retracted and extended again while the x-ray unit R is simultaneously swiveled. The control unit can be embodied such that a presettable pressure of the ultrasound unit US on the predetermined body region of the patient PT is kept constant. If the patient PT has to move unpredictably, this movement is absorbed by the securing system integrated into the coupling unit KE, for instance consisting of a monitoring of the spring pressure and a mechanical emergency tripping device, as far as a variance which can be preset individually to the patient. If the pressure of the ultrasound unit US on the patient PT becomes larger, tripping mechanisms in the active connecting element unit WVE are activated and the coupling unit KE detaches from the docking station connected to it on the positioning unit P or x-ray unit R. During the ultrasound examination the ultrasound unit US can be swiveled or tilted in a controlled manner by the physician, while the pressure on the patient PT remains the same. If the contact pressure of the ultrasound unit US changes to above a contact pressure which can be determined by the physician, either the active connecting element unit WVE opens between the first and second fastening unit BE1, BE2 or the control unit controls all electronic motors of the positioning unit P such that at least individual components are moved back by the positioning unit P or each of the hinges is released and these can be deflected in a predetermined direction or in all directions almost without resistance. In a further embodiment of the coupling unit KE, provision can be made for the second hollow cylinder Z2 to be entirely insertable into the first hollow cylinder Z1 when there is increased pressure from the ultrasound unit US on the patient PT. The second hollow cylinder is embodied as a sliding element GE. Furthermore, the first fastening unit BE1 could be embodied such that the second fastening unit BE2 is additionally received hereby. In a further embodiment variant a control unit can be embodied with control functions for the ultrasound unit US so that with this a straight scanning, tilting or swiveling can be carried out automatically. Guidance of the ultrasound unit US over a predetermined trajectory is likewise possible.

Figure 3:
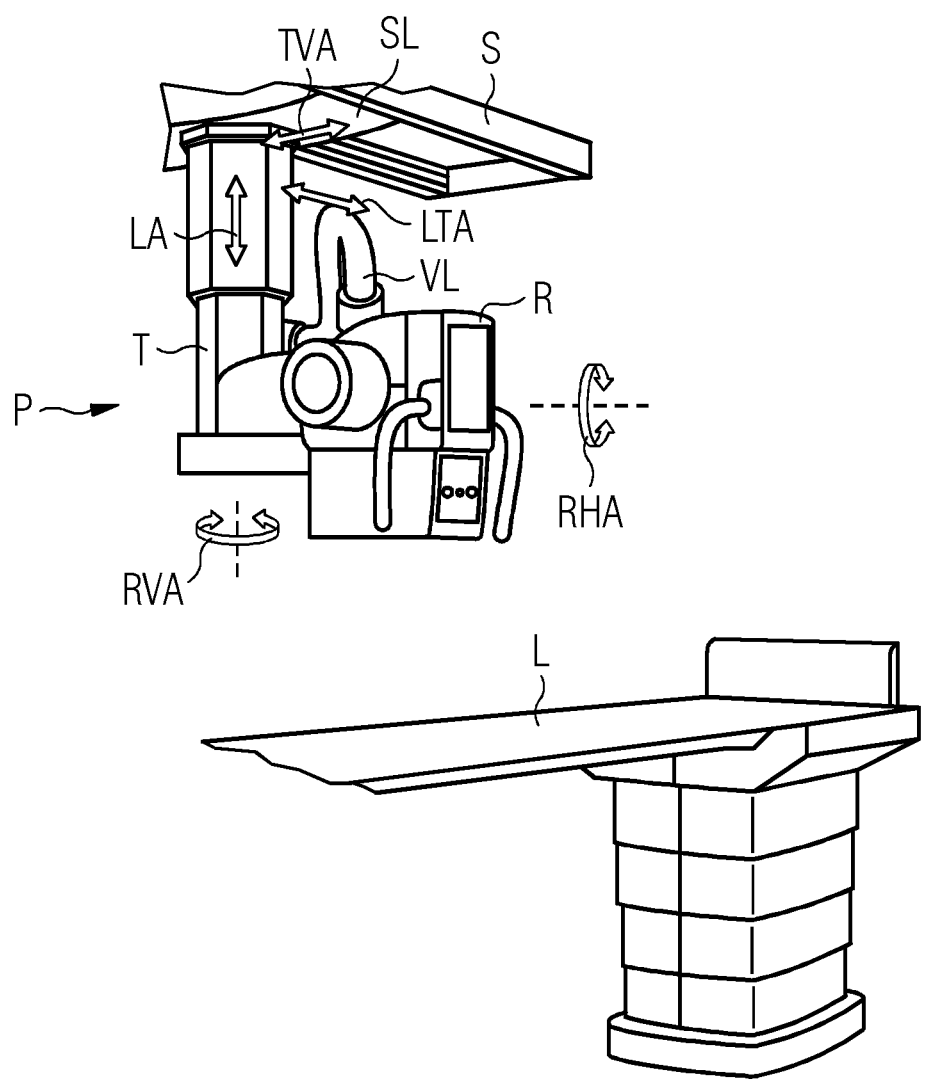
FIG. 3 is a perspective view of an x-ray unit.

FIG. 3 shows an x-ray unit R fastened to a ceiling rail S. Corresponding to the x-ray unit R which can be positioned above the ceiling rail S, a height-adjustable and pivotable couch L, for instance with a detector unit, can be positioned. For precise positioning for an individual recording or a plurality of recordings during a trajectory of the x-ray unit R or the ultrasound unit US which can be fastened on the x-ray unit R, FIG. 3 indicates the corresponding axes for aligning the x-ray device R or the ultrasound unit US. The positioning and alignment of the x-ray unit R or the ultrasound unit US is carried out using a positioning unit P. In this view, the controllable axes required to position and align the x-ray unit R or ultrasound unit US are indicated. In this embodiment variant, an alignable unit having a plurality of controllable axes is arranged at the end of the telescopic arm T. Using this unit, a horizontal rotation RHA and for instance a vertical rotation about the telescopic axis RVA can be carried out. The x-ray unit R is fastened to this unit. The x-ray or ultrasound unit R arranged on the telescopic arm T can be adjusted in terms of length or height using the telescopic arm T, indicated by the vertical arrow LA. The telescopic arm T can be moved both longitudinally LTA and also transversally TVA on a carriage SL. The carriage SL can be positioned at any point along the rails S.

Figure 4:
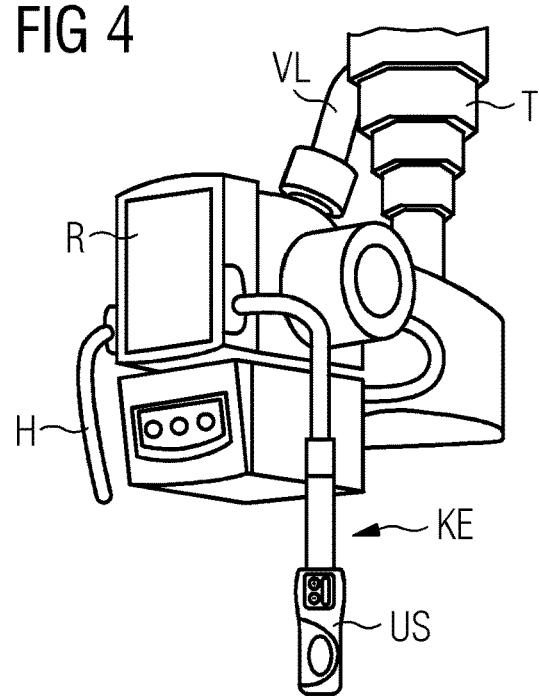
FIG. 4 is a perspective view of the device combination.

FIG. 4 shows a partial cutout of the ceiling-suspended x-ray unit R. A guide element H is provided on this x-ray unit R for its manual or semi-manual guidance or alignment. The guide element H can be arranged on both sides of the x-ray unit R. A coupling element KE attached to an ultrasound unit US can be embodied at its end such that with this a force closure on elements, for instance a guide element H, the x-ray unit R and/or on a docking station of the unit described below in FIG. 3 is enabled at the end of the telescopic arm T of the positioning unit P. Aside from the guide element H as a docking element, further fastening units can be provided or embodied for the coupling unit KE of the ultrasound unit HS on the chassis or the diaphragm unit of the x-ray unit R and/or the positioning unit P.

Figure 5:
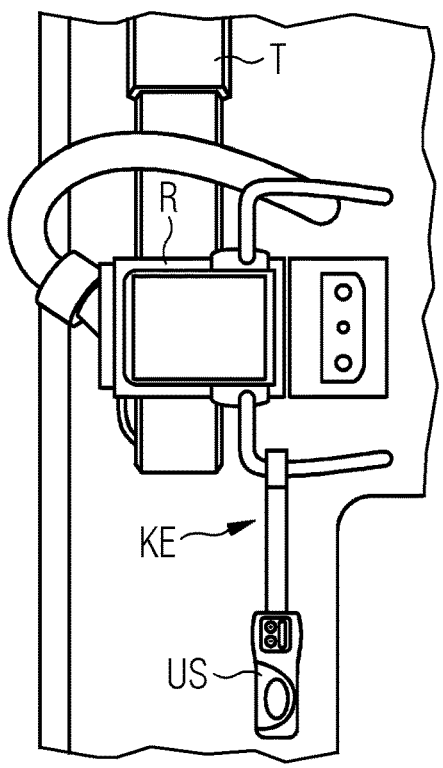
FIG. 5 is a further perspective view of the device combination.

FIG. 5 shows a further fastening variant on the guide element H of the x-ray unit R for the coupling element KE for guiding the ultrasound unit US.

The following is a summary list of reference numerals and the corresponding structure used in the above description of the invention:
US ultrasound unit
PT object, patient
L couch unit
SL carriage
S rail
T telescopic arm
VL supply lines
R x-ray unit
P positioning unit
LA arrow for height-adjustable telescopic arm
TVA transversal translation
LTA longitudinal translation
RHA horizontal rotation
RVA vertical rotation about the telescopic axis
F spring
KE coupling element
Z1 first hollow body
Z2 second hollow body
H guide element
KS force sensor
GE sliding element
MOE mechanical opening element
BE1 first fastening element
BE2 second fastening element
WVE active connecting element unit

The invention claimed is:

1. A device, comprising:
an x-ray machine for producing x-ray recordings of an object;
an ultrasound machine for producing ultrasound recordings of the object
an alignable positioner configured for:
aligning said x-ray machine with the object, and
aligning said ultrasound machine with the object such that:
said ultrasound machine is positioned on the object by using said aligning said x-ray machine with the object, and
guidance of said ultrasound machine is accomplished by using kinematics of said x-ray machine and said alignable positioner,
a coupling unit, said ultrasound machine and said x-ray machine being in a positionally fixed relationship to each other via said coupling unit, said ultrasound machine and said x-ray machine being positioned simultaneously via said alignable positioner; and
said coupling unit being formed with a first fastener and/or a second fastener, and a detachable connection with elements of said x-ray machine and/or said alignable positioner can be produced with said first fastener or said second fastener;
said first fastener and/or said second fastener of said coupling unit having sensor elements for monitoring a contact pressure of said ultrasound machine on the object to be examined, and when a predeterminable contact pressure of said ultrasound machine on the object to be examined is exceeded by a monitored contact pressure of said ultrasound machine on the object to be examined, said coupling unit becomes separated from said x-ray machine or said alignable positioner.

2. The device according to claim 1, wherein said alignable positioner has a controller, said controller generating control pulses for electric motors to be controlled on axes of said alignable positioner.

3. A method for producing x-ray recordings of an object with an x-ray machine, which comprises the steps of:
aligning the x-ray machine with the object using an alignable positioner;
connecting an ultrasound machine for producing ultrasound recordings to a coupling unit on the alignable positioner and/or the x-ray machine and is aligned with the object, the coupling unit positionally fixing the ultrasound machine relative to the x-ray machine and/or the alignable positioner;
positioning the ultrasound machine on the object using the alignable positioner for the x-ray machine, and guiding the ultrasound machine by using kinematics of the alignable positioner for the x-ray machine, and simultaneously positioning the ultrasound machine and the x-ray machine via the alignable positioner; and
introducing a separation of the fixing of the ultrasound machine to the x-ray machine and/or the alienable positioner when contact pressure of the ultrasound machine on the object exceeds a predeterminable contact pressure of the ultrasound machine on the object.

* * * * *